United States Patent [19]
Place

[11] Patent Number: 5,820,587
[45] Date of Patent: Oct. 13, 1998

[54] METHOD AND KIT FOR PREVENTING ERECTILE DYSFUNCTION

[75] Inventor: Virgil A. Place, Kawaihae, Hi.

[73] Assignee: Vivus Incorporated, Mountain View, Calif.

[21] Appl. No.: 819,620

[22] Filed: Mar. 17, 1997

Related U.S. Application Data

[63] Continuation of Ser. No. 403,333, Mar. 14, 1995, abandoned.

[51] Int. Cl.⁶ .................................................. A61M 31/00
[52] U.S. Cl. .............................. 604/54; 604/73; 514/968; 206/438
[58] Field of Search .................... 128/898; 604/19.48, 604/99.54, 73; 206/438, 803, 828; 600/38; 514/968

[56] References Cited

U.S. PATENT DOCUMENTS

| | | | |
|---|---|---|---|
| 3,797,493 | 3/1974 | Saudek | 206/828 X |
| 3,826,828 | 7/1974 | Morel . | |
| 4,127,118 | 11/1978 | Lattore | 128/79 |
| 4,311,707 | 1/1982 | Birnbaum et al. . | |
| 4,334,543 | 6/1982 | Fehr . | |
| 4,485,821 | 12/1984 | Linuma . | |
| 4,585,005 | 4/1986 | Lue et al. | 128/419 R |
| 4,612,937 | 9/1986 | Miller . | |
| 4,801,587 | 1/1989 | Voss | 514/268 |
| 4,828,544 | 5/1989 | Lane et al. | 604/9 |
| 4,889,238 | 12/1989 | Batchelor | 206/828 X |
| 5,059,603 | 10/1991 | Rubin . | |
| 5,148,920 | 9/1992 | Walker | 206/438 X |
| 5,219,885 | 6/1993 | Frölich et al. . | |
| 5,242,391 | 9/1993 | Place et al. | 604/60 |
| 5,399,581 | 3/1995 | Laragh | 514/396 |
| 5,474,535 | 12/1995 | Place et al. | 604/60 |
| 5,482,039 | 1/1996 | Place | 128/653.1 |
| 5,492,911 | 2/1996 | Stief | 514/968 |

FOREIGN PATENT DOCUMENTS

| | | |
|---|---|---|
| 0 357 581 A1 | 3/1990 | European Pat. Off. . |
| 0 459 666 A2 | 12/1991 | European Pat. Off. . |
| WO 90/02545 | 3/1990 | WIPO . |
| WO 91/16021 | 9/1991 | WIPO . |
| WO 93/00894 | 1/1993 | WIPO . |

OTHER PUBLICATIONS

The Merck Index, Prostaglandin citations, 1983, pp. 1134–1135, Oct. 1983.
Krane et al., "Medical Progress: Impotence," *The New England Journal of Medicine* 321(24):1628–1639 (1989).
T. I–Sheng Hwang et al., "Impotence Evaluated by the Use of Prostaglandin E1," *The Journal of Urology* 141:1357–1359 (1989).
Steif et al., "Mid–term results of autoinjection therapy for erectile dysfunction," *Urology* 31(6):483–485 (1988).
R. Virag et al., "Intracavernous Injection of Papaverine as a Diagnostic and Therapeutic Method in Erectile Failure," *Angiology—Journal of Vascular Diseases*, Feb. 1984, pp. 79–87.

*Primary Examiner*—Mark Bockelman
*Attorney, Agent, or Firm*—Dianne E. Reed; Bozicevic & Reed LLP

[57] ABSTRACT

A method is provided for preventing erectile dysfunction, particularly vasculogenic impotence, in a male individual. The method involves periodic administration of a vasoactive agent throughout a 24-hour period. The agent and dosage regimen are selected such that regularly increased blood flow to the penis is achieved, in turn preventing arterial occlusion and vascular deterioration of the muscular fibers of the vessels and collagen fibers of the cavernosal tissue.

59 Claims, 1 Drawing Sheet

METHOD AND KIT FOR PREVENTING ERECTILE DYSFUNCTION

This application is a continuation of application Ser. No. 08/403,333 filed Mar. 14, 1995, now abandoned.

TECHNICAL FIELD

This invention relates generally to the prevention of erectile dysfunction. More particularly, the invention relates to a novel procedure for preventing vasculogenic erectile dysfunction, e.g., vasculogenic impotence, by administering a selected vasoactive agent within the context of a predetermined dosing regimen. The invention also relates to a kit which an individual patient may use in the course of drug administration.

BACKGROUND

Impotence is the consistent inability to achieve or sustain an erection of sufficient rigidity for sexual intercourse. It has recently been estimated that approximately 10 million American men are impotent (R. Shabsigh et al., "Evaluation of Erectile Impotence," *Urology* 32:83–90 (1988); W. L. Furlow, "Prevalence of Impotence in the United States," *Med. Aspects Hum. Sex.* 19:13–6 (1985)). Impotence is recognized to be an age-dependent disorder, with an incidence of 1.9 percent at 40 years of age and 25 percent at 65 years of age (A. C. Kinsey et al., "Age and Sexual Outlet," in *Sexual Behavior in the Human Male,* A. C. Kinsey et al., eds., Philadelphia, Pa.: W. B. Saunders, 218–262 (1948)). In 1985 in the United States, impotence accounted for more than several hundred thousand outpatient visits to physicians (National Center for Health Statistics, National Hospital Discharge Survey, 1985, Bethesda, Md., Department of Health and Human Services, 1989 DHHS publication no. 87–1751). Depending on the nature and cause of the problem, treatments include psychosexual therapy, hormonal therapy, administration of vasodilators such as nitroglycerin and α-adrenergic blocking agents ("α-blockers"), oral administration of other pharmaceutical agents, vascular surgery, implanted penile prostheses, vacuum constriction devices and external aids such as penile splints to support the penis or penile constricting rings to alter the flow of blood through the penis.

A number of causes of impotence have been identified, including vasculogenic, neurogenic, endocrinologic and psychogenic. Impotence can also be a side effect of various classes of therapeutic drugs, or can be associated with various diseases, including diabetes, multiple sclerosis and sickle cell anemia. Impotence resulting from any one of these causes can be exacerbated by additional factors such as cigarette smoking, a poor diet, or the like.

Vasculogenic impotence occurs either as a result of arterial occlusion—the obstruction of adequate blood flow to the penile arteries necessary for erection—or as a result of cavernovenous leakage, i.e., excess venal outflow. As explained by Krane et al., "Medical Progress: Impotence," *The New England Journal of Medicine* 321(24):1628–1639 (1989), alteration in the flow of blood to and from the penis is believed to be the most frequent organic cause of impotence.

The present invention obviates the need for treatment of erectile dysfunction in a number of cases, insofar as a method is now provided which will substantially prevents the occurrence of vasculogenic impotence. The method involves periodic administration of a vasoactive agent as will be described below, within the context of a predetermined dosing regimen effective to provide for regularly increased blood flow to the penis. The invention additionally relates to kits which may be used in conjunction with the novel prophylactic method.

SUMMARY OF THE INVENTION

Accordingly, it is a primary object of the present invention to address the aforementioned need in the art, by providing a novel method for preventing the occurrence of erectile dysfunction.

It is another object of the invention to provide a method for preventing erectile dysfunction which involves administering to a patient, within the context of a predetermined dosing regimen, a selected vasoactive agent.

It is still another object of the invention to provide such a method in which the vasoactive agent is administered transurethrally.

It is yet another object of the invention to provide such a method in which the erectile dysfunction is vasculogenic impotence.

It is a further object of the invention to provide such a method in which the vasoactive agent is administered in conjunction with a transurethral permeation enhancer.

It is yet a further object of the invention to provide a kit which an individual patient may use to conduct the aforementioned method.

Additional objects, advantages and novel features of the invention will be set forth in part in the description which follows, and in part will become apparent to those skilled in the art upon examination of the following, or may be learned by practice of the invention.

In a first aspect of the invention, a vasoactive agent is administered to a patient in the context of a predetermined dosing regimen, such that drug is administered periodically throughout a 24-hour period. The drug is preferably administered transurethrally. It has now been found that regular administration of such an agent, preferably transurethrally, is effective to substantially prevent vasculogenic impotence. While not wishing to be bound by theory, it is proposed that periodic administration of a vasoactive drug, by regularly increasing blood flow to the penis, not only prevents arterial occlusion but also prevents vascular deterioration of the muscular fibers of the vessels and collagen fibers of the cavernosal tissue. It has also been found that administration of vasoactive agents in this manner may be conducted at doses which are lower than those which are normally necessary with such drugs, i.e., when used for their previously known indications.

In another aspect of the invention, a kit is provided to assist a patient in drug administration. Generally, the kit will include the following components: the drug to be administered; a device for administering the drug, e.g., a transurethral administration device; a sealed container housing the drug and device prior to use; and written instructions for drug administration. The kit may include a means for administering the drug at different doses, or it may include different drugs.

DETAILED DESCRIPTION OF THE INVENTION

Figure 1:
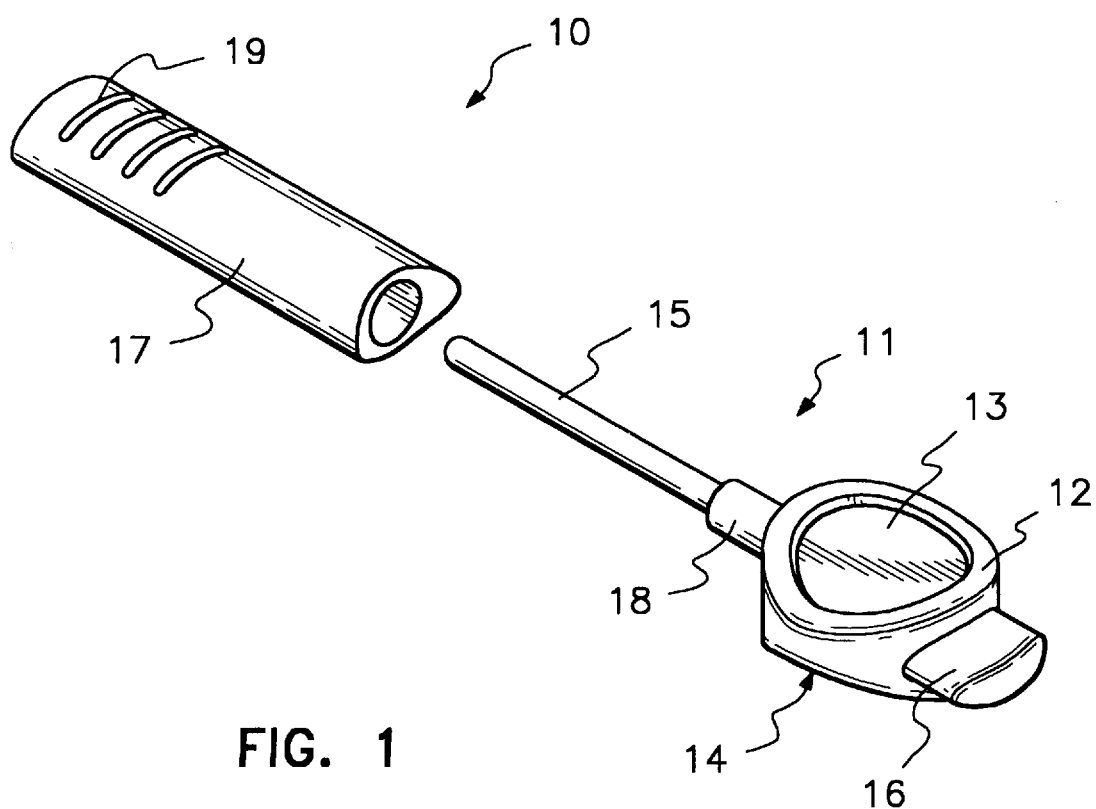
FIG. 1 is an exploded view of one embodiment of a transurethral therapeutic device which may be used in conjunction with the present method.

Before describing the present invention in detail, it is to be understood that this invention is not limited to particular drugs or drug delivery systems, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "a vasoactive agent" includes a mixture of two or more such drugs, reference to "a transurethral permeation enhancer" includes mixtures of two or more enhancers, and the like.

In describing and claiming the present invention, the following terminology will be used in accordance with the definitions set out below.

The term "drug" or "pharmacologically active agent" as used herein is intended to mean a compound or composition of matter which, when administered to an organism (human or animal) induces a desired pharmacologic and/or physiologic effect by local and/or systemic action. As noted above, the pharmacologically active agents used in conjunction with the present invention are vasoactive agents.

The terms "transurethral" or "intraurethral" as used to specify the mode of administration of vasoactive are used interchangeably to refer to delivery of the drug into the urethra such that drug contacts and passes through the wall of the urethra and enters into the blood stream.

By "transdermal" drug delivery, applicant is using the term in its conventional sense, i.e., to indicate delivery of a drug by passage through the skin and into the blood stream. By "transmucosal" drug delivery, applicant intends delivery of a drug by passage of a drug through the mucosal tissue into the blood stream. Aspects of the invention which are described in the context of "transurethral" drug delivery, unless otherwise specified, can apply to transdermal or transmucosal delivery as well. That is, the compositions, systems, and methods of the invention, unless explicitly stated otherwise, should be presumed to be equally applicable with any one of these three modes of drug delivery.

"Penetration enhancement" or "permeation enhancement" as used herein relates to an increase in the permeability of the skin or mucosal tissue to a selected pharmacologically active agent, i.e., so that the rate at which the drug permeates through the skin or mucosal tissue is increased. "Transurethral permeation enhancers" increase the permeability of the urethral wall to drugs administered as described herein.

"Carriers" or "vehicles" as used herein refer to carrier materials suitable for transurethral drug administration, and include any such materials known in the art, e.g., any liquid, gel, solvent, liquid diluent, solubilizer, or the like, which is nontoxic and which does not interact with other components of the composition in a deleterious manner.

By an "effective" amount of a drug or pharmacologically active agent is meant a nontoxic but sufficient amount of the drug or agent to provide the desired effect.

In order to carry out the method of the invention, a selected vasoactive agent is administered periodically throughout a twenty-four hour period. Suitable vasoactive agents include, but are not limited to: nitrates such as nitroglycerin, isosorbide dinitrate, erythrityl tetranitrate, amyl nitrate, sodium nitroprusside, molsidomine, linsidomine chlorhydrate ("SIN-1") and S-nitroso-N-acetyl-d,l-penicillamine ("SNAP"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; trazodone; naturally occurring prostaglandins such as $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptides. Prazosin, prostaglandin $E_1$ and prostaglandin $E_2$ are particularly preferred vasoactive agents for use in conjunction with the present method.

Additionally, simultaneous administration of two or more vasoactive agents may be desirable and may in some cases exhibit a synergistic effect. The combination of prazosin with prostaglandin $E_1$ has been found to be particularly advantageous in this regard; the latter drug appears to act a permeation enhancer for prazosin, i.e., it increases the rate at which prazosin permeates through the skin or mucosal tissue and enters the bloodstream.

The vasoactive agent will typically be administered in a pharmaceutical composition containing one or more selected carriers or excipients, as noted above. Examples of suitable carriers for use herein include water, silicone, waxes, petroleum jelly, polyethylene glycol, propylene glycol, liposomes, sugars such as mannitol and lactose, and a variety of other materials. The composition may also include one or more permeation enhancers, i.e., compounds which act to increase the rate at which the selected drug permeates through the skin or mucosal tissue. Examples of suitable permeation enhancers include dimethylsulfoxide (DMSO), dimethyl formamide (DMF), N,N-dimethylacetamide (DMA), decylmethylsulfoxide ($C_{10}$MSO), polyethylene glycol monolaurate (PEGML), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), alcohols, or the like.

The amount of vasoactive agent administered is selected to provide for regularly increased blood flow to the penis, such that arterial occlusion is prevented, as is vascular deterioration of the muscle fibers of the vessels and collagen fibers of the cavernosal tissue. Each individual dose is selected, in general, so as to produce tumescence, i.e., penile engorgement, but not necessarily rigidity. Suitable doses of selected drugs will be apparent to those skilled in the art, or may be deduced from the literature in combination with the teaching of the present disclosure. However, it should be noted that the selected drug is preferably administered 2 to 6 times in a twenty-four hour period. Generally, a lower dose of vasoactive agent will be required than is typically necessary for the usual indication of such a drug, i.e., as an antihypertensive agent or the like. For prazosin, for example, administration of 100 to 400 μg/dose, preferably 1 to 10 mg/day, most preferably 0.5 to 5 mg/day, is preferred. For other drugs, generally 25% to 50% of the indicated daily dosage for use as an antihypertensive agent is appropriate. See the *Physicians' Desk Reference®*, 48th Edition, Medical Economics Data Production Company (Montvale, N.J., 1994).

Transurethral administration of the drug is preferred although not essential. As explained in co-pending patent application Ser. No. 07/514,397, entitled "Treatment of Erectile Dysfunction" (published internationally as WO91/16021), the disclosure of which is incorporated by reference herein, transurethral administration of a drug can be carried out in a number of different ways. For example, the drug can be introduced into the urethra from a flexible tube, squeeze bottle, pump or aerosol spray. The drug may also be contained in coatings, pellets or suppositories which are absorbed, melted or bioeroded in the urethra. In certain embodiments, the drug is included in a coating on the exterior surface of a penile insert. A preferred drug delivery device for administering a drug transurethrally is shown in FIG. 1.

In FIG. 1, a transurethral drug delivery device is shown generally at 10. The device comprises a transurethral inserter 11 having an easily graspable segment 12 that has opposing symmetrically concave surfaces 13 and 14 adapted to be held by two fingers. Drug is contained within shaft 15, which is sized to fit within the urethra. A longitudinal plunger, the tip of which is seen at 16, is slidably insertable into the longitudinal bore contained within shaft 15. To extrude drug into the urethra, shaft 15 is inserted into the urethra, and plunger tip 16 is pushed into segment 12. The inserter 11 is then removed. Prior to use, and during storage, the device is capped with elongate cap 17 which fits snugly over flange 18 at the proximal end of shaft 15. The cap 17 is provided with a series of parallel ridges 19 to facilitate gripping of the cap and removal from inserter 11.

Although the configuration shown in FIG. 1 is a preferred configuration, other inserter/container configurations can be used and any mechanism by which a predetermined quantity of drug can be introduced from the inserter at a predetermined depth in the urethra is suitable for use with this invention. Examples of other such devices are those described and illustrated in WO91/16021, incorporated by reference above. The devices can either be manufactured under sterile conditions, thereby eliminating the need for post-manufacturing sterilization, or they can be manufactured under nonsterile conditions and then subsequently sterilized by any suitable technique, e.g., radiation sterilization. The devices can be manufactured by typical plastic forming and coating processes known in the art, including molding extrusion, heat forming, dip coating, and the like.

The vasoactive agent may also be administered topically, transdermally or by any other available and effective means. Transdermal drug administration, as is well known to those skilled in the art, involves the delivery of a pharmaceutical agent via percutaneous passage of the drug into the systemic circulation of the patient. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1–3, Kydonieus and Berner (eds.), CRC Press, (1987).

A variety of types of transdermal patches may be used in the method described herein. For example, a simple adhesive patch can be used which is prepared from a backing material and an acrylate adhesive. The adhesive layer is formulated so that drug, and any carriers or enhancers which are to be used, are contained therein. Alternatively, a hydrogel matrix patch can be used in which drug, water and, typically, hydrophilic polymers, are used to form a hydrogel, which is then incorporated into a transdermal patch between the backing and the adhesive layer. As will be appreciated by those skilled in the art, a number of other types of patch configurations can be used as well, including liquid reservoir patches, foam matrix patches, and the like. See, e.g., U.S. Pat. Nos. 3,598,122, 4,649,075 and 5,120,544, the disclosures of which are incorporated by reference herein.

Other components may be incorporated into such transdermal patches as well. For example, compositions and/or transdermal patches may be formulated with one or more preservatives or bacteriostatic agents, e.g., methyl hydroxybenzoate, propyl hydroxybenzoate, chlorocresol, benzalkonium chloride, or the like.

The invention also encompasses a kit for patients to carry out the aforementioned prophylactic method. The kit contains the drug to be administered, a device for administering the drug, preferably transurethrally (e.g., as shown in FIG. 1), a sealed container housing the drug and device prior to use, and written instructions for drug administration. The kit may include a means for administering the drug at different doses, or it may include different drugs, or a combination thereof. (That is, if the drug as initially administered is not effective, incrementally higher doses of drug can be used, or alternative drugs may be administered.)

The method of the invention accordingly provides effective prophylactic therapy, in that the occurrence of erectile dysfunction, particularly vasculogenic impotence, is substantially prevented in most patients.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

EXAMPLE 1

Patients with a tendency toward vasculogenic impotence, such as patients who have recently undergone a radical prostatectomy, are given 0.3 mg prazosin hydrochloride every four hours throughout a 24-hour period. After several days to several weeks, various penile hemodynamic parameters are measured and compared with corresponding parameters evaluation prior to drug therapy. These parameters will typically include cavernosal artery peak systolic velocity, cavernosal artery end diastolic velocity, maximum arterial dilation, and pressure. Based on these measurements, a determination is made as to whether penile vascular sufficiency is present. It will be appreciated by those skilled in the art that any number of devices can be used to conduct the aforementioned measurements, providing that the desired level of accuracy is achieved. Duplex ultrasonography is the preferred mode of evaluating the penile hemodynamic parameters of interest. However, other types of techniques and equipment may be used as well, e.g., NMR spectroscopy, pressure cuffs, corpus cavernosograms, angiography, NPT (nocturnal penile tumescence) "Rigiscans," magnetic resonance imaging (MRI), computer aided tomography (CAT), pulsoximeters, and the like.

Examples of duplex ultrasonography devices which can be used in conjunction with the present method include those described in U.S. Pat. Nos. 4,334,543 to Fehr, 4,485,821 to Iinuma, and 4,612,937 to Miller, the disclosures of which are incorporated by reference herein. Suitable devices are available from a number of manufacturers, including, for example, Advanced Technology Laboratories (Bothell, Wash.) and Siemens Quantum (Issaquah, Wash.).

Based on the hemodynamic parameters measured using the aforementioned ultrasonography technique, a diagnosis can be made as to penile vascular sufficiency. Generally, if the measured PSV is less than about 50 cm/sec, more typically less than about 35 cm/sec, vascular inflow is insufficient, and a diagnosis of arterial insufficiency may be made. Alternatively, or additionally, if the measured EDV is greater than 0 cm/sec, more typically greater than about 5 cm/sec, a diagnosis of venous leakage may be made. It is expected that after the aforementioned drug therapy, the penile hemodynamic measurements which are conducted will lead to a finding of penile vascular sufficiency.

EXAMPLE 2

The procedure of Example 1 is repeated, except that drug is administered every six hours instead of every four hours, with dosage adjusted accordingly. Substantially the same results are expected.

EXAMPLE 3

The procedure of Example 1 is repeated, except that drug is administered every eight hours instead of every four hours, with dosage adjusted accordingly. Substantially the same results are expected.

EXAMPLE 4

The procedure of Example 1 is repeated, except that drug is administered every twelve hours instead of every four hours, with dosage adjusted accordingly. Substantially the same results are expected.

EXAMPLE 5

The procedure of Example 1 is repeated, except that prazosin base is substituted for prazosin hydrochloride. Substantially the same results are expected.

EXAMPLE 6

The procedure of Example 5 is repeated, except that drug is administered every six hours instead of every four hours, with dosage adjusted accordingly. Substantially the same results are expected.

EXAMPLE 7

The procedure of Example 5 is repeated, except that drug is administered every eight hours instead of every four hours, with dosage adjusted accordingly. Substantially the same results are expected.

EXAMPLE 8

The procedure of Example 5 is repeated, except that drug is administered every twelve hours instead of every four hours, with dosage adjusted accordingly. Substantially the same results are expected.

EXAMPLE 9

The procedure of Example 1 is repeated, except that prostaglandin $E_1$ is substituted for prazosin, at a dose of approximately 3.0 $\mu$g/kg body weight. Substantially the same results are expected.

EXAMPLE 10

The procedure of Example 9 is repeated, except that drug is administered every six hours instead of every four hours, with dosage adjusted accordingly. Substantially the same results are expected.

EXAMPLE 11

The procedure of Example 9 is repeated, except that drug is administered every eight hours instead of every four hours, with dosage adjusted accordingly. Substantially the same results are expected.

EXAMPLE 12

The procedure of Example 9 is repeated, except that drug is administered every twelve hours instead of every four hours, with dosage adjusted accordingly. Substantially the same results are expected.

EXAMPLE 13

The procedure of Example 1 is repeated, except that prostaglandin $E_2$ is substituted for prazosin, at a dose of approximately 5 mg. Substantially the same results are expected.

EXAMPLE 14

The procedure of Example 13 is repeated, except that drug is administered every six hours instead of every four hours, with dosage adjusted accordingly. Substantially the same results are expected.

EXAMPLE 15

The procedure of Example 13 is repeated, except that drug is administered every eight hours instead of every four hours, with dosage adjusted accordingly. Substantially the same results are expected.

EXAMPLE 16

The procedure of Example 13 is repeated, except that drug is administered every twelve hours instead of every four hours, with dosage adjusted accordingly. Substantially the same results are expected.

I claim:

1. A method for preventing vasculogenic impotence in a male individual, comprising administering to the urethra of the individual a pharmaceutical composition comprising a vasoactive agent, within the context of a dosing regimen effective (a) to provide for regularly increased blood flow to the penis, (b) to prevent arterial occlusion, and (c) to prevent deterioration of the muscle fibers and collagen fibers due to vascular loss, wherein the vasoactive agent comprises a prostaglandin and the dosing regimen comprises regular administration of a predetermined dose of the vasoactive agent two to six times in a twenty-four hour period, with the time intervals between each dose administration being substantially identical, and further wherein each dose is effective to produce penile tumescence.

2. The method of claim 1, wherein drug administration is carried out by placing the pharmaceutical composition in contact with the male urethra at a location between the proximal portion of the fossa navicularis and the distal portion of the pendulous urethra, such that the vasoactive agent contained in the composition enters the individual's blood stream through the urethral wall.

3. The method of claim 2, wherein the agent is administered in a dispersant which releases the agent in the urethra at said location at a weight ratio of dispersant to agent of about 1:1 to 50:1, the amount of said dose not exceeding the dose retaining capacity of the urethra.

4. The method of claim 3, wherein the amount of agent and dispersant that is administered transurethrally is approximately 50 mg.

5. The method of claim 1, wherein a transurethral permeation enhancer is administered with the vasoactive agent.

6. The method of claim 5, wherein the transurethral permeation enhancer and vasoactive agent are administered simultaneously.

7. The method of claim 5, wherein the transurethral permeation enhancer and vasoactive agent are administered sequentially.

8. The method of claim 1, wherein the predetermined dose is administered three to six times in a twenty-four hour period.

9. The method of claim 1, wherein the pharmaceutical composition comprises an additional vasoactive agent.

10. The method of claim 1, wherein the prostaglandin is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, carboprost tromethamine, dinoprost tromethamine, dinoprostone, lipoprost, gemeprost, metenoprost, sulprostone and tiaprost.

11. The method of claim 10, wherein the pharmaceutical composition comprises an additional vasoactive agent.

12. The method of claim 10, wherein the prostaglandin is $PGE_1$.

13. The method of claim 12, wherein the pharmaceutical composition comprises an additional vasoactive agent.

14. The method of claim 10, wherein the prostaglandin is $PGE_2$.

15. The method of claim 14, wherein the pharmaceutical composition comprises an additional vasoactive agent.

16. The method of any one of claims 9, 11, 13 or 15, wherein the additional vasoactive agent is selected from the group consisting of antihypertensive agents, nitrates, long- and short-acting $\alpha$-blockers, calcium blockers, ergot alkatoids, chlorpromazine, haloperidol, yohimbine, natural and synthetic vasoactive prostaglandins and their analogs, vasoactive intestinal peptides, dopamine agonists, opioid antagonists, and combinations thereof.

17. The method of claim 16, wherein the additional vasoactive agent is an antihypertensive agent.

18. The method of claim 17 wherein the antihypertensive agent is prazosin.

19. A kit for preventing vasculogenic erectile dysfunction in a male individual, comprising: a pharmaceutical composition comprising a vasoactive agent effective to increase blood flow to the penis; a drug delivery means for administering the pharmaceutical composition transurethrally; a container for housing the composition and drug delivery means; and written instructions for using the drug delivery means for administering a dose of the vasoactive agent transurethrally two to six times in a twenty-four hour period, with the time intervals between each dose being substantially identical, and wherein the vasoactive agent comprises a prostaglandin and each dose is effective to produce penile tumescence.

20. The kit of claim 19, wherein the written instructions specify administering the agent three to six times in a twenty-four hour period.

21. The kit of claim 19, wherein the pharmaceutical composition further comprises a transurethral permeation enhancer.

22. The kit of claim 19, wherein the prostaglandin is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, carboprost tromethamine, dinoprost tromethamine, dinoprostone, lipoprost, gemeprost, metenoprost, sulprostone and tiaprost.

23. The kit of claim 22, wherein the prostaglandin is $PGE_1$.

24. The kit of claim 22, wherein the prostaglandin is $PGE_2$.

25. The kit of claim 19, wherein the pharmaceutical composition comprises an additional vasoactive agent.

26. The kit of claim 22, wherein the pharmaceutical composition comprises an additional vasoactive agent.

27. The kit of claim 23, wherein the pharmaceutical composition comprises an additional vasoactive agent.

28. The kit of claim 24, wherein the pharmaceutical composition comprises an additional vasoactive agent.

29. The kit of any one of claims 25, 26, 27 or 28, wherein the additional vasoactive agent is selected from the group consisting of antihypertensive agents, nitrates, long- and short-acting $\alpha$-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and combinations thereof.

30. The kit of claim 29, wherein the additional vasoactive agent is an antihypertensive agent.

31. The kit of claim 30, wherein the antihypertensive agent is prazosin.

32. A method for preventing vasculogenic impotence, comprising administering to a male individual having penile vascular insufficiency but not having vasculogenic impotence a pharmaceutical composition comprising a vasoactive agent, within the context of a dosing regimen effective (a) to provide for regularly increased blood flow to the penis, (b) to prevent arterial occlusion, or (c) to prevent deterioration of the muscle fibers and collagen fibers due to vascular loss, wherein the dosing regimen comprises regular administration of a predetermined dose of the vasoactive agent two to six times in a twenty-four hour period, with the time intervals between each dose administration being substantially identical.

33. The method of claim 32, wherein the vasoactive agent is administered transurethrally.

34. The method of claim 33, wherein a transurethral permeation enhancer is administered with the vasoactive agent.

35. The method of claim 34, wherein the transurethral permeation enhancer and the vasoactive agent are administered simultaneously.

36. The method of claim 34, wherein the transurethral permeation enhancer and the vasoactive agent are administered sequentially.

37. The method of claim 33, wherein drug administration is carried out by placing the vasoactive agent in contact with the male urethra at a location between the proximal portion of the fossa navicularis and the distal portion of the pendulous urethra, such that the vasoactive agent enters the individual's blood stream through the urethral wall.

38. The method of claim 37, wherein the agent is administered in a dispersant which releases the agent in the urethra at said location at a weight ratio of dispersant to agent of about 1:1 to 50:1, the amount of said dose not exceeding the dose retaining capacity of the urethra.

39. The method of claim 38, wherein the amount of agent and dispersant that is administered transurethrally is approximately 50 mg.

40. The method of claim 32, wherein the vasoactive agent is selected from the group consisting of antihypertensive agents, nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and combinations thereof.

41. The method of claim 40, wherein the vasoactive agent is a prostaglandin.

42. The method of claim 41, wherein the vasoactive agent is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, carboprost tromethamine, dinoprost tromethamine, dinoprostone, lipoprost, gemeprost, metenoprost, sulprostone and tiaprost.

43. The method of claim 40, wherein a combination of vasoactive agents is administered.

44. The method of claim 43, wherein the combination comprises an antihypertensive agent and a prostaglandin.

45. The method of claim 44, wherein the combination comprises prazosin and prostaglandin $E_1$.

46. The method of claim 44, wherein the combination comprises prazosin and prostaglandin $E_2$.

47. A kit for preventing vasculogenic erectile dysfunction, comprising: a vasoactive agent effective to increase blood flow to the penis; a drug delivery means for administering the vasoactive agent; a container for housing the agent and drug delivery means; and written instructions for using the drug delivery means for administering the vasoactive agent two to six times in a twenty-four hour period to a male individual having penile vascular insufficiency but not having vasculogenic impotence, with the time intervals between each dose being substantially identical.

48. The kit of claim 47, wherein the drug delivery means is used for administering the agent transurethrally.

49. The kit of claim 47, wherein the vasoactive agent is selected from the group consisting of antihypertensive agents, nitrates, long- and short-acting α-blockers, calcium blockers, ergot alkaloids, chlorpromazine, haloperidol, yohimbine, natural and synthetic vasoactive prostaglandins and their analogs, vasoactive intestinal peptides, dopamine agonists, opioid antagonists, and combinations thereof.

50. The kit of claim 49, wherein the vasoactive agent is a prostaglandin or prostaglandin analog.

51. The kit of claim 50, wherein the vasoactive agent is selected from the group consisting of $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$, carboprost tromethamine, dinoprost tromethamine, dinoprostone, lipoprost, gemeprost, metenoprost, sulprostone and tiaprost.

52. The kit of claim 51, wherein the vasoactive agent is $PGE_1$.

53. The kit of claim 51, wherein the vasoactive agent is $PGE_2$.

54. The kit of claim 50, wherein the pharmaceutical composition comprises an additional vasoactive agent.

55. The kit of claim 51, wherein the pharmaceutical composition comprises an additional vasoactive agent.

56. The kit of claim 52, wherein the pharmaceutical composition comprises an additional vasoactive agent.

57. The kit of claim 53, wherein the pharmaceutical composition comprises an additional vasoactive agent.

58. The kit of any one of claims 54, 55, 56 or 57, wherein the additional vasoactive agent is an antihypertensive agent.

59. The kit of claim 58, wherein the antihypertensive agent is prazosin.

* * * * *